United States Patent
Salamone et al.

(10) Patent No.: US 6,805,836 B2
(45) Date of Patent: Oct. 19, 2004

(54) PREVENTION OF PRESERVATIVE UPTAKE INTO BIOMATERIALS

(75) Inventors: Joseph C. Salamone, Boca Raton, FL (US); Daniel M. Ammon, Jr., Rochester, NY (US); Zhenze Hu, Pittsford, NY (US)

(73) Assignee: Bausch & Lomb Incorporated, Rochester, NY (US)

( * ) Notice: Subject to any disclaimer, the term of this patent is extended or adjusted under 35 U.S.C. 154(b) by 0 days.

(21) Appl. No.: 09/738,808

(22) Filed: Dec. 15, 2000

(65) Prior Publication Data

US 2002/0114729 A1 Aug. 22, 2002

(51) Int. Cl.⁷ .................................................. A61L 2/00
(52) U.S. Cl. ............................ 422/1; 422/5; 422/28; 422/29; 422/40; 523/106; 523/107
(58) Field of Search .................... 422/1, 40, 5, 28, 422/29; 523/106, 107

(56) References Cited

U.S. PATENT DOCUMENTS

| | | | |
|---|---|---|---|
| 4,136,250 A | 1/1979 | Mueller et al. ............... 528/29 |
| 4,153,641 A | 5/1979 | Deichert et al. ............. 260/827 |
| 4,168,112 A | 9/1979 | Ellis et al. ................... 351/160 |
| 4,321,261 A * | 3/1982 | Ellis et al. ................... 424/180 |
| 4,354,952 A | 10/1982 | Riedhammer et al. ...... 252/106 |
| 4,436,730 A | 3/1984 | Ellis et al. ................... 424/180 |
| 4,442,125 A * | 4/1984 | Thiele ......................... 424/318 |
| 4,463,149 A | 7/1984 | Ellis ............................ 526/279 |
| 4,604,479 A | 8/1986 | Ellis ............................ 556/440 |
| 4,686,267 A | 8/1987 | Ellis et al. ................... 526/245 |
| 4,740,533 A | 4/1988 | Su et al. ...................... 523/106 |
| 4,758,595 A | 7/1988 | Ogunbiyi et al. ............ 514/635 |
| 4,786,436 A | 11/1988 | Ogunbiyi et al. ........... 252/352 |
| 4,826,936 A | 5/1989 | Ellis ............................ 526/258 |
| 4,954,587 A | 9/1990 | Mueller ....................... 526/245 |
| 4,992,536 A * | 2/1991 | Billmers et al. ............. 536/120 |
| 4,996,275 A | 2/1991 | Ellis et al. ................... 526/245 |
| 5,010,141 A | 4/1991 | Mueller ....................... 525/276 |
| 5,032,658 A | 7/1991 | Baron et al. ................. 526/321 |
| 5,034,461 A | 7/1991 | Lai et al. ..................... 525/100 |
| 5,070,215 A | 12/1991 | Bambury et al. ............ 556/418 |
| 5,079,319 A | 1/1992 | Mueller .................. 526/238.23 |
| 5,177,165 A | 1/1993 | Valint, Jr. et al. ........... 526/245 |
| 5,177,168 A | 1/1993 | Baron et al. ................. 526/321 |
| 5,219,965 A | 6/1993 | Valint, Jr. et al. ........... 526/245 |
| 5,260,000 A | 11/1993 | Nandu et al. ................. 264/2.1 |
| 5,310,779 A | 5/1994 | Lai ............................. 524/588 |
| 5,321,108 A | 6/1994 | Kunzler et al. .............. 526/242 |
| 5,336,797 A | 8/1994 | McGee et al. ............... 556/419 |
| 5,346,976 A | 9/1994 | Ellis et al. ................... 526/279 |
| 5,358,995 A | 10/1994 | Lai et al. ..................... 524/547 |
| 5,364,918 A | 11/1994 | Valint, Jr. et al. ........... 526/245 |
| 5,387,662 A | 2/1995 | Kunzler et al. .............. 526/245 |
| 5,401,327 A * | 3/1995 | Ellis et al. ..................... 134/42 |
| 5,405,878 A | 4/1995 | Ellis et al. ..................... 422/28 |
| 5,449,729 A | 9/1995 | Lai ............................. 526/286 |
| 5,453,435 A | 9/1995 | Raheja et al. ................ 514/402 |
| 5,500,144 A | 3/1996 | Potini et al. ............. 252/174.15 |
| 5,512,205 A | 4/1996 | Lai ......................... 252/182.14 |
| 5,604,189 A | 2/1997 | Zhang ......................... 510/407 |
| 5,610,252 A | 3/1997 | Bambury et al. ............ 526/279 |
| 5,616,757 A | 4/1997 | Bambury et al. ............ 556/419 |
| 5,708,094 A | 1/1998 | Lai ............................. 525/296 |
| 5,710,302 A | 1/1998 | Kunzler et al. .............. 556/434 |
| 5,711,823 A | 1/1998 | Ellis et al. ..................... 134/42 |
| 5,714,557 A | 2/1998 | Kunzler et al. .............. 526/279 |
| 5,760,100 A * | 6/1998 | Nicolson et al. ............ 523/106 |
| 5,773,396 A | 6/1998 | Zhang et al. ................ 510/115 |
| 5,858,937 A | 1/1999 | Richard et al. .............. 510/112 |
| 5,872,086 A | 2/1999 | Ellis et al. ................... 510/112 |
| 5,908,906 A | 6/1999 | Kunzler et al. .............. 526/279 |
| 5,965,631 A * | 10/1999 | Nicolson et al. ............ 523/106 |
| 5,981,669 A | 11/1999 | Valint, Jr. et al. ........... 525/477 |

FOREIGN PATENT DOCUMENTS

| | | | |
|---|---|---|---|
| EP | 0888770 A1 | 7/1999 | ............ A61K/9/00 |
| GB | 1 432 345 | 4/1972 | ......... A61K/31/785 |
| WO | WO 95/00618 | 1/1995 | |
| WO | WO 95/00620 | 1/1995 | |
| WO | WO 00/37048 | 6/2000 | |

* cited by examiner

*Primary Examiner*—Krisanne Thornton
(74) *Attorney, Agent, or Firm*—Robert B. Furr, Jr.; John E. Thomas; Rita D. Vacca

(57) ABSTRACT

A method for inhibiting the ability of a biomaterial to sorb cationic antimicrobials comprising treating the surface of said biomaterial with a cationic polysaccharide.

19 Claims, No Drawings

PREVENTION OF PRESERVATIVE UPTAKE INTO BIOMATERIALS

FIELD OF THE INVENTION

The present invention is directed to the surface treatment of medical devices including ophthalmic lenses, stents, implants and catheters. In particular, the present invention is directed to a simple, low cost method of modifying the surface of a medical device to decrease its capacity to sorb cationic antimicrobials.

BACKGROUND

Medical devices such as ophthalmic lenses can generally be subdivided into two major classes, namely hydrogels and non-hydrogels. Non-hydrogels do not absorb appreciable amounts of water, whereas hydrogels can absorb and retain water in an equilibrium state.

Hydrogels are widely used as soft contact lens materials. It is known that increasing the hydrophilicity of the contact lens surface improves the wettability of the contact lenses. This in turn is associated with improved wear comfort of contact lenses. Additionally, the surface of the lens can affect the overall susceptibility of the lens to deposition of proteins and lipids from the tear fluid during lens wear. Accumulated deposits can cause eye discomfort or even inflammation. In the case of extended wear lenses (i.e. lenses used without daily removal of the lens before sleep), the surface is especially important, since extended wear lenses must be designed for high standards of comfort and biocompatibility over an extended period of time.

Both daily-wear lenses and extended-wear lenses need to be periodically cleaned and disinfected. Formulating multi-purpose solutions that not only clean and disinfect but are also ophthalmically compatible has proven to be a significant technical challenge. It has also been found that some contact lenses become less ophthalmically compatible with repeated cycles of wearing and cleaning. While the presence of lipid and protein deposits are important factors in predicting comfort, the presence or absence of these deposits alone fails to account for the observation that fresh contact lenses are typically more comfortable in the eye than lenses that have undergone one or more cleaning/disinfection cycles. Thus the cleaning and disinfection cycle appears to cause lenses to become progressively less comfortable, and the reduction in ocular comfort appears not to be attributable to imperfect cleaning.

In the area of contact lens wetting/conditioning solutions, it has been found that polyelectrolytes can bind to a lens surface of opposite charge and form polyelectrolyte complexes. Such polyelectrolyte complexes have commercially been demonstrated to give more comfortable lens materials because of the greater adsorption of surface bound water. Examples of materials useful for forming such polyelectrolyte complexes are taught in U.S. Pat. No. 4,321,261 to Ellis et al.; U.S. Pat. No. 4,436,730 to Ellis et al.; U.S. Pat. No. 5,401,327 to Ellis et al.; U.S. Pat. No. 5,405,878 to Ellis et al.; U.S. Pat. No. 5,500,144 to Potini et al.; U.S. Pat. No. 5,604,189 to Zhang et al; U.S. Pat. No. 5,711,823 to Ellis et al.; U.S. Pat. No. 5,773,396 to Zhang et al.; and U.S. Pat. No. 5,872,086 to Ellis et al.

The following references provide examples of typical contact lens care solutions. British Patent 1,432,345 discloses contact lens disinfecting compositions containing a polymeric biguanide and a mixed phosphate buffer.

U.S. Pat. No. 4,758,595 to Ogunbiyi et al. disclosed that a contact-lens solution containing a polyaminopropyl biguanide (PAPB) has enhanced efficacy when combined with a borate buffer. Such solutions are compatible with both non-soft and soft-type lenses, and are adaptable for use with virtually any of the commonly known disinfecting techniques, including "cold" soaking under ambient temperature conditions, as well as with high temperature disinfecting methods. These disinfecting and preservative solutions are especially noteworthy for their broad spectrum of bactericidal and fungicidal activity at low concentrations coupled with very low toxicity when used with soft-type contact lenses. Ogunbiyi et al. stated that biguanide polymers in the higher molecular weight ranges usually demonstrate lower toxicity levels than the lower molecular weight materials.

U.S. Pat. No. 5,453,435 to Raheja et al. discloses a preservative system that comprises a combination of chlorhexidine and the biguanide polymer polyhexamethylene biguanide. This preservative system, used in commercial products for rigid-gas-permeable lenses, was found to exhibit a combination of improved efficacy and relatively low eye irritation.

Compositions containing PAPB and borate, or other non-phosphate buffers, have been commercialized in various products, but at levels of about 1 ppm or less for use with soft contact lenses. It is generally desirable to provide the lowest level of a bactericide possible, while maintaining the desirable level of disinfection efficacy, in order to provide a generous margin for safety and comfort.

Some of the most popular products for disinfecting lenses are multipurpose solutions that can be used to clean, disinfect and wet contact lenses, followed by direct insertion (placement on the eye) without rinsing. The ability to use a single solution for contact-lens care is an advantage. Such a solution, however, must be particularly gentle to the eye because some of the solution will be on the lens when inserted and will come into contact with the eye.

Contact lens solutions that qualify as a "Chemical Disinfecting Solution" do not require rubbing to meet performance criteria set by the US Food and Drug Administration (FDA) under the Premarket Notification (510 k) Guidance Document For Contact Lens Care Produce, May 1, 1997, for destroying bacteria and fungi. However, they would generally require a more efficacious or stronger antimicrobial than a solution that requires rubbing. It is generally true that the stronger the bactericidal effect of a solution the more likely that it may exhibit toxic effects or adversely affect lens-wearer comfort. In fact, many very efficacious bactericides used in other contexts, such as mouthwashes, cosmetics, or shampoos, while being sufficiently safe for use in such products, are too toxic for ophthalmic use, especially for use with soft lenses because of the above-mentioned tendency of soft lenses to bind chemicals and the sensitivity of eye tissues. Similarly, the concentrations of certain bactericides may need to be within lower limits in solutions for use with soft contact lenses than in other products or in solutions for other types of lenses, especially when such solutions are not rinsed from the contact lens before placing the lens in the eye. Thus one way to decrease ocular irritation is to use a lower concentration of antimicrobial in solution, provided that the concomitant decrease in antimicrobial efficacy is acceptable. It would also be desirable to decrease ocular irritation without decreasing the concentration of antimicrobial in solution or its disinfecting efficacy.

Certain antibacterial agents have been found to be more compatible with contact lenses and exhibit less binding on lens surfaces. In one case, it was found that chlorhexidine, a biguanide, binds to soft lens material seven times less than benzalkonium chloride, but the presence of proteinaceous oily tear-film deposits on a lens can double the amount of chlorhexidine absorbed on the lens compared to a clean lens. U.S. Pat. No. 4,354,952 discloses very dilute disinfecting and cleaning solutions containing chlorhexidine or its salts in combination with certain amphoteric and non-ionic surfactants. These solutions were found to reduce the amount of binding of chlorhexidine on hydrophilic soft contact lenses.

Thus it would be desirable to inhibit the extent to which contact lenses, especially hydrogel contact lenses, progressively sorb antimicrobials during repeated cleaning/disinfection steps. Inhibiting sorption of antimicrobials by the contact lens during the cleaning/disinfection step would then decrease the amount of antimicrobial available to be desorbed from the contact lenses into the tear film when the lenses are returned to the wearer's eyes. Such an improvement would enhance the long-term comfort of biomaterials (such as contact lens materials) that must be periodically cleaned and disinfected.

SUMMARY OF THE INVENTION

This invention provides a method for cleaning and disinfecting biomaterials that have the ability to reversibly sorb cationic antimicrobials. These biomaterials appear to accumulate antimicrobials when they are in contact with a solution having an antimicrobial concentration sufficient to drive sorption of the antimicrobial to the biomaterials. Then when the biomaterials contact an aqueous solution having lower antimicrobial concentrations, they desorb the antimicrobial over a period of time as the positively charged, ionically bound antimicrobial is released from the lens by displacement from endogenic ions in the tear film. The antimicrobial sorption behavior of hydrogel materials is of particular interest because hydrogels are commonly used as biomaterials, especially as contact lens materials.

This invention provides a method for inhibiting the ability of a biomaterial to sorb cationic antimicrobials. In one embodiment, the method of the invention comprises treating the surface of the biomedical material with a cationic polysaccharide. The surface of the biomaterial is preferably at least slightly anionic.

In another embodiment of the invention, the surface of the biomaterial may carry a net neutral charge or a net cationic charge, and the biomaterial may be treated with a linking agent to initially coat the surface of the biomaterial in order to present a net anionic charge prior to the treatment with the cationic polysaccharide.

Thus the invention provides a method for inhibiting the ability of a biomaterial to sorb antimicrobials comprising binding a cationic polysaccharide to the surface of the biomaterial. As used herein, the term "binding" refers to forming a relatively stable complex or other relatively stable attraction between the surface of a biomaterial and a polysaccharide with or without the addition of a linking agent, and is not limited to a particular mechanism. Thus "binding" may involve covalent bonds, hydrogen bonds, hydrophobic interactions or other molecular interactions that enable the cationic polysaccharide of the invention to form a relatively tenacious surface coating on a biomaterial. While not to limit the scope of the present invention by a recitation of theory, the method of inhibiting the deposition of the antimicrobial on the lens by cationic polysaccharide appears to be related to the polycation being bound to available anionic sites on the biomaterial because of its greater charge density, thus preventing the sorption of the lower molecular weight, cationic antimicrobials. Additionally, or potentially, if the cationic antimicrobial is sorbed to the anionic biomaterial, it is possible that the cationic polysaccharide will displace the cationic antimicrobial because of its greater binding efficiency caused by its greater charge density. Both situations would thus lower the concentration of sorbed cationic antimicrobial on a biomaterial.

The method may further comprise treating the surface of the biomaterial to provide a net anionic charge on the surface before contacting said surface with said cationic polysaccharide. In one embodiment of the method of the invention, the biomaterial carries a net anionic surface charge and no intermediate treatment step is needed to modify the surface charge before binding said polysaccharide to the surface of the biomaterial. In another embodiment, the method includes contacting the surface of the biomaterial with a linking agent.

The method may employ different mechanisms for binding the cationic polysaccharide on the surface of the biomaterial. Examples of binding mechanisms include bonds such as ionic interactions, hydrogen-bonded interactions, hydrophobic interactions and covalent interactions. If the cationic polysaccharide is bound to the surface of the biomaterial through ionic interations, those ionic interactions are suitably between oppositely charged ionic groups on the biomaterial and the cationic polysaccharide contained in an aqueous solution. If the surface of the biomaterial has a net negative charge, that negative charge may be derived from at least one selected from the group consisting of carboxylate groups, sulfonate groups, sulfonate groups, phosphate groups, phosphinate groups and phosphonate groups. The cationic charge on the cationic polysaccharide may be derived from ammonium groups, quaternary ammonium groups, sulfonium groups, phosphonium groups, and other positively charged functional groups.

The method of the invention may also bind the cationic polysaccharide to the surface of the biomaterial through hydrogen-bonding interactions. These hydrogen-bonding interactions may occur between hydrogen-bond accepting surfaces and hydrogen-bond donating solutions, or between hydrogen-bond donating surfaces and hydrogen-bond accepting solutions. Examples of hydrogen-bond accepting groups include pyrrolidone groups, N,N-disubstituted acrylamide groups and polyether groups. Examples of suitable polyether groups include poly(ethylene glycol) or poly (ethylene oxide. Examples of suitable hydrogen-donating groups include carboxylic acids, phosphoric acids, phosphonic acids and phenolic groups.

The cationic polysaccharide may also attach to the surface of the biomaterial through interactions between hydrophobic sites on the biomaterial surface and interacting hydrophobic groups on the cationic polysaccharide. Covalent interactions may also exist between the biomaterial surface and the water-soluble cationic polysaccharide such that the cationic polysaccharide is bound to the biomaterial surface.

The biomaterial may be an ophthalmic lens, for example an intraocular lens or a contact lens. If the biomaterial is an ophthalmic lens, the lens is preferably fabricated from a material having a net anionic surface charge, either by bulk inclusion of anionic sites or by surface treatment.

Examples of useful cationic polysaccharides include those polysaccharides derived from the families based on cellulosics, guar gum, starch, dextran, chitosan, locust bean gum, gum tragacanth, curdlan, pullulan and seleroglucan. Of particular interest are the cationic polymers derived from cellulosic materials. It is believed that the degree of inhibition activity is related to the strength of the ionic bonding between the polymeric surface coating and the lens surface. Thus, stronger bonds are believed to enhance the desired inhibition effects.

The invention also provides a solution for disinfecting and/or cleaning contact lenses. The solution preferably comprises from about 0.1 to about 20 ppm of a biguanide antimicrobial; 0.05 to 2.5 weight percent of a buffer such as borate, phosphate, citrate, bicarbonate, tromethamine and mixtures thereof; 0.01 to 15 weight percent of a surfactant such as a poloxamer, poloxamine, polysorbate-20 and tyloxapol. Alternatively, the maximum concentration of the buffer in solution is an amount sufficient to provide the necessary buffering action while maintaining acceptable solution tonicity.

The solution further comprises one or more tonicity adjusting agents selected from the group consisting of inorganic salts, low molecular weight polyols, mono- and di-saccharides in concentration sufficient to provide solution osmolality of from about 200 to about 400 mOsm/kg.

The solution of the invention preferably comprises from 0.2 to 10 ppm of a biguanide antimicrobial; 0.1 to 1.5 weight percent of a buffer; 0.1 to 5 weight percent of a surfactant; and one or more tonicity adjusting agents in concentration sufficient to provide solution osmolality of 250 to 350 mOsm/kg.

The solution of the invention more preferably comprises from 0.3 to 5 ppm of a biguanide antimicrobial; 0.15 to 1 weight percent of a buffer; 0.4 to 2 weight percent of a surfactant; and one or more tonicity adjusting agents in concentration sufficient to provide solution osmolality of 280 to 320 mOsm/kg.

DETAILED DESCRIPTION OF THE INVENTION

Examples of biomaterials useful in the present invention are taught in U.S. Pat. Nos. 5,908,906 to Künzler et al.; 5,714,557 to Künzler et al.; 5,710,302 to Künzler et al.; 5,708,094 to Lai et al.; 5,616,757 to Bambury et al.; 5,610,252 to Bambury et al.; 5,512,205 to Lai; 5,449,729 to Lai; 5,387,662 to Künzler et al. and 5,310,779 to Lai; which patents are incorporated by reference as if set forth at length herein.

Rigid gas-permeable (RGP) materials typically comprise a hydrophobic cross-linked polymer system containing less than 5 wt. % water. RGP materials useful in accordance with the present invention include those materials taught in U.S. Pat. Nos. 4,826,936 to Ellis; 4,463,149 to Ellis; 4,604,479 to Ellis; 4,686,267 to Ellis et al.; 4,826,936 to Ellis; 4,996,275 to Ellis et al.; 5,032,658 to Baron et al.; 5,070,215 to Bambury et al.; 5,177,165 to Valint et al.; 5,177,168 to Baron et al.; 5,219,965 to Valint et al.; 5,336,797 to McGee and Valint; 5,358,995 to Lai et al.; 5,364,918 to Valint et al.; 5,610,252 to Bambury et al.; 5,708,094 to Lai et al; and 5,981,669 to Valint et al. U.S. Pat. No. 5,346,976 to Ellis et al. teaches a preferred method of making an RGP material.

The invention is applicable to a wide variety of contact lens materials, and anionic contact lens materials, either rigid or soft, are particularly preferred. Hydrogels comprise hydrated, cross-linked polymeric systems containing water in an equilibrium state. Such hydrogels could be silicone hydrogels, which generally have a water content greater than about five weight percent and more commonly between about ten to about eighty weight percent. Such materials are usually prepared by polymerizing a mixture containing at least one silicone-containing monomer and at least one hydrophilic monomer. Applicable silicone-containing monomeric units for use in the formation of silicone hydrogels are well known in the art and numerous examples are provided in U.S. Pat. Nos. 4,136,250; 4,153,641; 4,740,533; 5,034,461; 5,070,215; 5,260,000; 5,310,779; and 5,358,995.

In particular regard to contact lenses, the fluorination of certain monomers used in the formation of silicone hydrogels has been indicated to reduce the accumulation of deposits on contact lenses made therefrom, as described in U.S. Pat. Nos. 4,954,587, 5,079,319 and 5,010,141. Moreover, the use of silicone-containing monomers having certain fluorinated side groups, i.e. —($CF_2$)—H, have been found to improve compatibility between the hydrophilic and silicone-containing monomeric units, as described in U.S. Pat. Nos. 5,387,662 and 5,321,108.

Other non-silicone hydrogels used for extended wear applications are also applicable, provided that surface attachment of the cationic polysaccharide can be achieved. Rigid gas-permeable lenses are of interest because many of these materials utilize methacrylic acid units for wetting. These acid units generate an anionic surface that can complex a cationic polysaccharide.

Surface coating materials useful in the present invention include cationic polysaccharides, for example cationic cellulosic polymers. Specific examples include cellulosic polymers containing N,N-dimethylaminoethyl groups (either protonated or quaternized) and cellulosic polymers containing N,N-dimethylamino-2-hydroxylpropyl groups (either protonated or quaternized). Cationic cellulosic polymers are commercially available or can be prepared by methods known in the art. As an example, quaternary nitrogen-containing ethoxylated glucosides can be prepared by reacting hydroxyethyl cellulose with a trimethylammonium-substituted epoxide. Various preferred cationic cellulosic polymers are commercially available, for example water-soluble polymers available under the CTFA (Cosmetic, Toiletry, and Fragrance Association) designation "Polyquaternium-10". Such polymers are commercially available under the trade name of UCARE® Polymer from Amerchol Corp., Edison, N.J., USA. These polymers contain quaternized N,N-dimethylamino groups along the cellulosic polymer chain.

The cationic cellulosic component may be employed in the compositions at about 0.01 to about ten (10) weight percent of the composition, preferably at about 0.02 to about five (5) weight percent, with about 0.05 to about one (1) weight percent being especially preferred. Suitable cationic cellulosic materials have the following formula:

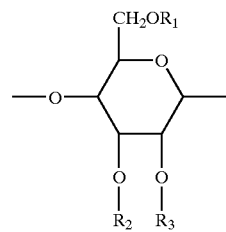

Wherein $R_1$ $R_2$ and $R_3$ are selected from H, derivatives of $C_1$–$C_{20}$ carboxylic acid, $C_1$–$C_{20}$ alkyl groups, $C_1$ to $C_3$ monohydric and dihydric alkanols, hydroxyethyl groups, hydroxypropyl groups, ethylene oxide groups, propylene oxide groups, phenyl groups, "Z" groups and combinations thereof. At least one of $R_1$, $R_2$, and $R_3$ is a Z group.

The nature of the "Z" groups is:

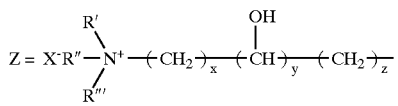

where:

R', R" and R'" can be H, $CH_3$, $C_2H_5$, $CH_2CH_2OH$ and

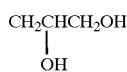

x=0–5, y=0–4, and z=0–5

$X^- = Cl^-$, $Br^-$, $I^-$, $HSO_4^-$, $CH_3SO_4^-$, $H_2PO_4^-$, $NO_3^-$

U.S. Pat. No. 5,645,827 to Marlin, et al. (incorporated by reference as if set forth at length herein for a discussion of cationic polysaccharides) discloses the use of compositions comprising a cationic polysaccharide in combination with an anionic therapeutic agent, for example, hyaluronic acid or its salt, which is a known demulcent for the treatment of dry eye. European Application 088770 A1 to Marlin et al. discloses cationic cellulose polymers to deliver cationic therapeutic agents, especially for the treatment of glaucoma. U.S. Pat. Nos. 4,436,730 and 5,401,327 to Ellis, et al. (which are incorporated by reference as if set forth at length herein) disclose the use of cationic cellulosic derivatives in contact-lens treating solutions, including the combination of a cationic cellulose polymer and an ethoxylated glucose such as glucam.

Optionally, one or more additional polymeric or non-polymeric demulcents may be combined with the above-named ingredients. Demulcents are known to provide wetting, moisturizing and/or lubricating effects, resulting in increased comfort. Polymeric demulcents can also act as a water-soluble viscosity builder. Included among the water-soluble viscosity builders are the non-ionic cellulosic polymers like methyl cellulose, hydroxyethyl cellulose, hydroxypropyl cellulose, and carboxymethyl cellulose, poly(N-vinylpyrrolidone), poly(vinyl alcohol) and the like. Such viscosity builders or demulcents may be employed in a total amount ranging from about 0.01 to about 5.0 weight percent or less. Suitably, the viscosity of the final formulation is 2 to 200 cps. Comfort agents such as glycerin or propylene glycol can also be added.

The solution used to treat the contact lenses in accordance with the invention contains a disinfecting amount of one or more cationic antimicrobial agents. Antimicrobial agents are defined as organic chemicals that derive their antimicrobial activity through a chemical or physiochemical interaction with the microbial organisms. Examples of cationic antimicrobials include those generally employed in ophthalmic applications and include, but are not limited to, quaternary ammonium salts such as benzalkonium halides, biguanides such as free bases or salts of alexidine and chlorhexidine, hexamethylene biguanides and their polymers, polyquaterniuml, cytolytic peptides such as dermaseptin, ceropin and melittin, and combinations of the foregoing. The salts of alexidine and chlorhexidine can be either organic or inorganic and are typically gluconates, nitrates, acetates, phosphates, sulfates, halides and the like. The preferred antimicrobial is biguanide and the preferred biguanide is the hexamethylene biguanide commercially available from Zeneca, Wilmington, Del. under the trademark Cosmocil™ CQ. Generally, the hexamethylene biguanide polymers, also referred to as polyaminopropyl biguanide (PAPB), have molecular weights of up to about 100,000.

If used in the subject solution, the antimicrobial agent should be used in an amount that will at least partially reduce the microorganism population in the formulations employed. Preferably, a disinfecting amount is an amount that will reduce the microbial bioburden by two log orders in four hours and more preferably by one log order in one hour. Most preferably, a disinfecting amount is an amount that will eliminate the microbial burden on a contact lens when used in regimen for the recommended soaking time (FDA Chemical Disinfection Efficacy Test-July, 1985 Contact Lens Solution Draft Guidelines). Typically, such agents are present in concentrations ranging from about 0.1 to about 0.5% (w/v), and more preferably, from about 0.00003 to about 0.05% (w/v).

The aqueous solutions employed in this invention may contain, in addition to the active ingredients described above, one or more other components that are commonly present in ophthalmic solutions, for example, buffers, stabilizers, tonicity agents and the like, which aid in making ophthalmic compositions more comfortable to the user. The aqueous solutions of the present invention are typically adjusted with tonicity agents to approximate the tonicity of normal lacrimal fluids which is equivalent to a 0.9% solution of sodium chloride or 2.8% of glycerol solution. The solutions are made substantially isotonic with physiological saline used alone or in combination; otherwise, if simply blended with sterile water and made hypotonic or made hypertonic, the lenses will lose their desirable optical parameters. Correspondingly, excess salt or other tonicity agents may result in the formation of a hypertonic solution that will cause stinging and eye irritation. An osmolality of about 250 to 350 mOsm/kg is preferred, more preferably 280 to 320 mOsm/kg.

The pH of the present solutions should be maintained within the range of 5.0 to 8.0, preferably about 6.0 to 8.0, more preferably about 6.5 to 7.5; suitable buffers may be added, such as borate, phosphate, citrate, bicarbonate, tromethamine and mixtures thereof. Borate buffers are preferred, particularly for enhancing the efficacy of PAPB. Generally, buffers will be used in amounts ranging from about 0.05 to 2.5 weight percent, and preferably from 0.1 to 1.5 percent, and more preferably, from 0.15 to 1 weight percent.

In addition to buffering agents, in some instances it may be desirable to include sequestering agents in the present solutions in order to bind metal ions, which might otherwise react with the lens and/or protein deposits and collect on the lens. Ethylene-diaminetetraacetic acid (EDTA) and its salts (disodium) are preferred examples. They are usually added in amounts ranging from about 0.01 to about 0.2 weight percent.

The solutions employed in the present invention can be prepared by a variety of techniques. One method employs two-phase compounding procedures. In the first phase, about 30 percent of the distilled water are used to dissolve the cationic polysaccharide by mixing for about 30 minutes at around 50° C. The first-phase solution is then autoclaved at about 120° C. for 30 minutes. In a second phase, alkali metal chlorides, sequestering agents, preservatives and buffering agents are then dissolved in about 60 percent of the distilled water under agitation, followed by the balance of distilled water. The second-phase solution can then be sterilely added into the first-phase solution by forcing it through a 0.22 micron filter by means of pressure, followed by packaging in sterilized plastic containers.

As indicated above, the present invention is useful for improving comfort and wearability for extended-wear contact lenses. For that purpose, compositions for use in the present invention may be formulated as eye-drops and sold in a wide range of small-volume containers from 1 to 30 ml in size. Such containers can be made from HDPE (high density polyethylene), LDPE (low density polyethylene), polypropylene, poly(ethylene terepthalate) and the like. Flexible bottles having conventional eye-drop dispensing tops are especially suitable for use with the present invention. The eye-drop formulation of the invention used by instilling, for example, about one (1) or three (3) drops in the eye(s) as needed.

The present invention is also useful as a component of a cleaning, disinfecting or conditioning solution. The invention may also include surfactants, either amphoteric or non-ionic, that are known to be useful components of conditioning and/or cleaning solutions for contact lenses. Examples of suitable formulations for cleaning and/or disinfecting solutions are taught in U.S. Pat. No. 5,858,937 to Richard and Heiler, which is incorporated by reference as if set forth at length herein.

EXAMPLES

Example 1

This example illustrates the binding effect of the cationic cellulosic polymer onto hydrophilic contact lenses. Three Surevue® lenses (manufactured by Johnson & Johnson, New Brunswick, N.J.) in three different solutions were submitted for comparison by Atomic Force Microscopy (AFM) analysis. Solution 1, for comparison, was a Blank Borate-Buffered Saline. Solution 2 was Solution 1 with 0.1% Polymer JR. Solution 3, for further comparison, was ReNu® MPS (manufactured by Bausch & Lomb, Rochester, N.Y.). The lenses were treated overnight, and then removed from the vials and desalinated in HPLC grade water in a static fashion for a minimum of 15 minutes. All lenses were cut with a clean scalpel on a clean glass substrate. The samples were dried, sectioned and placed on a clean substrate. Three 50×50 µm topographical images were acquired for each side (anterior and posterior) of the lenses using AFM. The AFM used in this study was the Dimension 3000 and was operated in ContactMode. The AFM works by measuring nano-scale forces ($10^{-9}$N) between a sharp probe and atoms on the lens surface. The resulting AFM images showed that the anterior and posterior surfaces of the lenses stored in Blank Borate-Buffered Saline (Solution 1) as well as ReNu® MPS (Solution 3) showed no significant topographical change. The anterior and posterior surfaces of the lenses stored in Polymer JR solution (Solution 2) showed a significantly different topography. The surface is covered with a thin film, with multi-sized and shaped voids covering both anterior and posterior surfaces. These voids had an average depth of 40±10 nm. These void-like anomalies were not present in the lenses stored in Solution 1 or Solution 3. The voids had an effect on the Root Mean Square (RMS) roughness for the lenses stored in the Polymer JR solution.

The RMS surface roughness was calculated using the Nanoscope software (shown in Table below). The lenses stored in Solution 1 or Solution 3 had a smoother anterior and posterior surface compared to the anterior and posterior of lenses stored in the Polymer JR solution.

TABLE 1

RMS Roughness for Each Set of AFM Images

| Solution | Anterior | Posterior | Mean |
|---|---|---|---|
| Solution 1 | 3.93 nm | 3.03 nm | 3.48 nm |
| Solution 2 | 8.85 nm | 6.21 nm | 7.53 nm |
| Solution 3 | 5.82 nm | 3.09 nm | 4.46 nm |

The AFM results shown above indicate that the cationic cellulosic polymer (Polymer JR) has an effect on the morphology of the lens surface, indicating a thin film covering with large multi-shaped and sized voids on the anterior and posterior side of the lens.

Example 2

Example 2 evaluates whether the addition of a cationic polysaccharide, Polymer JR, to a preserved solution could reduce the uptake of that preservative into Surevue® contact lenses. Two preservatives were studied: alexidine and PHMB. UV analysis was carried out.

Method and Materials

UV-VIS absorbance spectra of the samples were determined on a Perkin Elmer Lambda 9 UV-VIS-NIR Spectrophotometer. The slit width utilized in the instrument resulted in a beam size of 10 mm high by 2 mm wide at the sample intercept. Quartz micro-cuvettes with a pathlength of 10 mm and a pathwidth of 4 mm were utilized to accommodate the small sample volumes. The appropriate solution was used in both cuvettes for the background run and in the reference cuvette for the sample scans.

The Perkin Elmer Lambda 9 UV-VIS-NIR Spectrophotometer was set up to the conditions shown below in Table 2.

TABLE 2

| Parameter | Setting |
|---|---|
| Scan Range (nm) | 400–190 |
| Slit (nm) | 2 |
| Scan Speed (nm/min) | 240 |
| Response (second) | 0.5 |
| Sample Mask | Not Installed |
| Data Interval (nm) | 1.0 |
| Data Mode | Absorbance |

Two buffers are examined with their compositions listed below:

Phosphate Buffer
0.016% sodium Phosphate (monobasic)
0.066% sodium Phosphate (dibasic)
0.88% Sodium Chloride
pH=7.26

Borate Buffer
1.0% Boric Acid
0.4% Sodium Chloride
0.11% Sodium Borate
pH=7.2

Results and Discussion

UV analysis was used to measure the absorbance of control alexidine and PHMB solutions. Both preservatives had a $\lambda_{max}$=235 nm. There were two control alexidine solutions. The first control solution contained alexidine only, at 0.004%. It had an absorbance of 1.43. The second control solution contained alexidine at 0.004% and Polymer JR at 0.1%. It had an absorbance of 1.67. Twelve Surevue® lenses were added to 10 mls of each control solution. After a four-hour soak, the UV absorbance was measured again. The control solution containing only alexidine and 12 Surevue® lenses had an absorbance of 0.13. The control solution containing alexidine, Polymer JR and twelve lenses had an absorbance of 0.28. There were also two control PHMB solutions. The first control solution contained PHMB at 0.002% and Polymer JR at 0.1%. It had an absorbance of 1.2. The second solution contained PHMB only. It also had an absorbance of 1.2. Twelve Surevue® lenses were added to 10 mls of each control solution. After a four-hour soak, the UV absorbance were measured again. The control solution containing only PHMB and 12 Surevue® lenses had an absorbance of 0.23. The control solution containing PHMB, Polymer JR and twelve lenses had an absorbance of 0.46. Table 3 converts the UV absorbance to micrograms in the presence of twelve lenses in the 10 ml of solution.

TABLE 3

|  | Absorbance | $\mu$gs in 10 mls |
|---|---|---|
| Alexidine | 0.13 | 36 |
| Alexidine + polymer JR | 0.28 | 78.3 |
| PHMB | 0.23 | 38.3 |
| PHMB + polymer JR | 0.46 | 76.7 |

Conclusion

The results showed that the addition of Polymer JR to a preserved solution reduced the uptake of PHMB and alexidine into Surevue® lenses.

Many other modifications and variations of the present invention are possible in light of the teachings herein. It is therefore understood that, within the scope of the claims, the present invention can be practiced other than as herein specifically described.

What is claimed is:

1. A method for treating a hydrogel biomaterial comprising contacting the surface of said hydrogel biomaterial with a cationic polysaccharide to inhibit the ability of the hydrogel biomaterial to sorb cationic antimicrobials.

2. The method of claim 1 further comprising treating the surface of said biomaterial to provide a net anionic charge on said surface before contacting said surface with said cationic polysaccharide.

3. The method of claim 1 wherein the surface of said biomaterial carries a net anionic surface charge and wherein the method includes no intermediate treatment step to modify the surface charge before binding said polysaccharide to the surface of said biomaterial.

4. The method of claim 2 wherein said surface treating step further comprises contacting said surface with a linking agent.

5. The method of claim 1 wherein said binding step futher comprises retaining said cationic polysaccharide on the surface of said biomaterial through at least one selected from the group consisting of ionic interactions, hydrogen-bonded interactions, hydrophobic interactions and covalent interactions.

6. The method of claim 5 wherein said ionic interactions are between oppositely charged ionic groups between the biomaterial and an aqueous solution containing the cationic polysaccharide.

7. The method of claim 6 wherein the negative charge on the biomaterial is derived from at least one selected from the group consisting of carboxylate groups, sulfonate groups, phosphate groups, phosphonate groups, sulfate groups, and phosphinate groups.

8. The method of claim 5 wherein said hydrogen-bonding interactions occur between hydrogen-bond accepting surfaces and hydrogen-bond donating solutions, or through hydrogen-bond donating surfaces and hydrogen-bond accepting surfaces.

9. The method of claim 8 wherein said hydrogen-bond accepting groups are selected from the group consisting of pyrrolidone groups, N,N-disubstituted acrylamide groups and polyether groups.

10. The method of claim 9 wherein said polyether groups are poly(ethylene glycol) or poly(ethylene oxide).

11. The method of claim 8 wherein said hydrogen-donating groups are selected from the group consisting of carboxylic acids, sulfonic acids, sulfuric acids, phosphoric acids, phosphonic acids and phenolic groups.

12. The method of claim 5 wherein said hydrophobic interactions occur through hydrophobic sites on the biomaterial surface interacting with hydrophobic groups on the cationic polysaccharide.

13. The method of claim 5 wherein said covalent interactions exist between the biomaterial surface and the water-soluble cationic polysaccharide such that the cationic polysaccharide is bound to the biomaterial surface.

14. The method of claim 1 wherein said biomaterial is an ophthalmic lens.

15. The method of claim 14 wherein said ophthalmic lens is a contact lens.

16. The method of claim 1 wherein said biomaterial is a silicone hydrogel material.

17. The method of claim 16 wherein said silicone hydrogel material is an extended-wear contact lens suitable for periods of continuous wear for about 7 to about 30 days.

18. The method of claim 1 wherein the cationic polysaccharide is selected from the group consisting of cationic starch, cationic dextran, cationic chitosan, cationic locust bean gum, cationic gum tragacanth, cationic curdlan, cationic pullulan and cationic scleroglucan.

19. The method of claim 6 wherein the cationic charge on the cationic polysaccharide is derived from at least one selected from the group consisting of ammonium groups, quaternary ammonium groups, sulfonium groups, and phosphonium groups.

* * * * *

UNITED STATES PATENT AND TRADEMARK OFFICE
CERTIFICATE OF CORRECTION

PATENT NO. : 6,805,836 B2
DATED : October 19, 2004
INVENTOR(S) : Joseph C. Salamone, et al.

It is certified that error appears in the above-identified patent and that said Letters Patent is hereby corrected as shown below:

Column 11,
Line 51, replace "futher" with -- further --.

Signed and Sealed this

Fifth Day of July, 2005

JON W. DUDAS
*Director of the United States Patent and Trademark Office*